(12) United States Patent
Myrick et al.

(10) Patent No.: US 9,377,424 B2
(45) Date of Patent: Jun. 28, 2016

(54) METHODS OF DETECTING LATENT STAINS ON A SURFACE

(71) Applicants: Michael Myrick, Columbia, SC (US); Wayne O'Brien, Ringgold, GA (US); Stephen L. Morgan, Columbia, SC (US); Briana Marie Cassidy, Columbia, SC (US); Raymond Gerard Belliveau, III, Columbia, SC (US); Zhenyu Lu, Columbia, SC (US)

(72) Inventors: Michael Myrick, Columbia, SC (US); Wayne O'Brien, Ringgold, GA (US); Stephen L. Morgan, Columbia, SC (US); Briana Marie Cassidy, Columbia, SC (US); Raymond Gerard Belliveau, III, Columbia, SC (US); Zhenyu Lu, Columbia, SC (US)

(73) Assignee: University of South Carolina, Columbia, SC (US)

( * ) Notice: Subject to any disclaimer, the term of this patent is extended or adjusted under 35 U.S.C. 154(b) by 350 days.

(21) Appl. No.: 14/158,075

(22) Filed: Jan. 17, 2014

(65) Prior Publication Data
US 2014/0198821 A1 Jul. 17, 2014

Related U.S. Application Data

(60) Provisional application No. 61/753,670, filed on Jan. 17, 2013, provisional application No. 61/779,638, filed on Mar. 13, 2013.

(51) Int. Cl.
*G01N 25/72* (2006.01)

(52) U.S. Cl.
CPC ................................... *G01N 25/72* (2013.01)

(58) Field of Classification Search
CPC .......... G01N 3/60; G01N 25/18; G01N 25/72
USPC ............................................. 374/5, 4, 43, 57
See application file for complete search history.

(56) References Cited

U.S. PATENT DOCUMENTS

| | | | | |
|---|---|---|---|---|
| 2007/0021670 A1* | 1/2007 | Mandelis | ............. | A61B 5/0088 600/473 |
| 2009/0245321 A1* | 10/2009 | Ringermacher | ....... | G01N 25/72 374/5 |
| 2011/0007774 A1* | 1/2011 | Hatcher | ................. | G01N 25/72 374/5 |
| 2011/0090342 A1* | 4/2011 | Myrick | ................... | G01J 3/433 348/164 |

\* cited by examiner

*Primary Examiner* — Lisa Caputo
*Assistant Examiner* — Nigel Plumb
(74) *Attorney, Agent, or Firm* — Dority & Manning, P.A.

(57) ABSTRACT

Methods for identifying chemical contrasts on a common surface are generally provided. The presence of a stain on a surface can be detected by applying a testing vapor, such as water, onto the surface and monitoring the surface with an infrared camera that detects wavelengths of about 700 nm to about 1 mm and/or a microbolometer that detects wavelengths of about 7.5 μm to about 14 μm. The surface may be at room temperature or preheated during the detection method.

20 Claims, 3 Drawing Sheets

METHODS OF DETECTING LATENT STAINS ON A SURFACE

PRIORITY INFORMATION

The present application claims priority to U.S. Provisional Patent Application Ser. No. 61/753,670 titled "Thermographic Imaging of Chemical Contrast via Differential Heating" of Myrick, et al. filed on Jan. 17, 2013 and to U.S. Provisional Patent Application Ser. No. 61/779,638 titled "Method of Detecting Latent Stains on a Surface" of Myrick, et al. filed on Mar. 13, 2013, both disclosures of which are incorporated by reference herein.

BACKGROUND

Stains that are not visible to the eye are often present on many types of surfaces. Detection of such stains, without affecting the surface, is an important process, especially in museums, forensic labs, textile industries, etc. Such stains can sometimes be located through the use of an ultraviolet light source (e.g., a black light) that emits light having a wavelength within a range 10 nm to 400 nm, depending on the composition and concentration of the stain and/or the surface.

However, not all stains are visible using detection currently known techniques. A need exists for detection of a latent stain on a surface when the nature of the stain composition and/or its concentration (e.g., relatively small) inhibits detection from other methods.

SUMMARY

Objects and advantages of the invention will be set forth in part in the following description, or may be obvious from the description, or may be learned through practice of the invention.

Methods are generally provided for detecting a chemical contrast on a surface. In one embodiment, the method includes heating the surface with a testing vapor from an initial temperature to a peak temperature; allowing the surface to cool from the peak temperature to the initial temperature; and monitoring the surface with a temperature measuring instrument during heating. Any portion of the surface that heats differently than the remaining portion of the surface indicates a stain is present.

In another embodiment, the method includes heating the surface with a vapor from an initial temperature to a peak temperature; allowing the surface to cool from the peak temperature to the initial temperature; and monitoring the surface with a temperature measuring instrument during cooling. Any portion of the surface that cools differently than the remaining portion of the surface indicates a stain is present.

In yet another embodiment, the method includes preheating the substrate to a testing temperature; exposing the substrate to a testing vapor; monitoring the surface of the substrate with a temperature measuring instrument during exposure to the testing vapor. Any portion of the surface that shows a thermal event different than the remaining portion of the surface indicates a stain is present.

Systems and apparatus are also generally provided that are configured to perform the methods described herein.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which.

Figure 1:
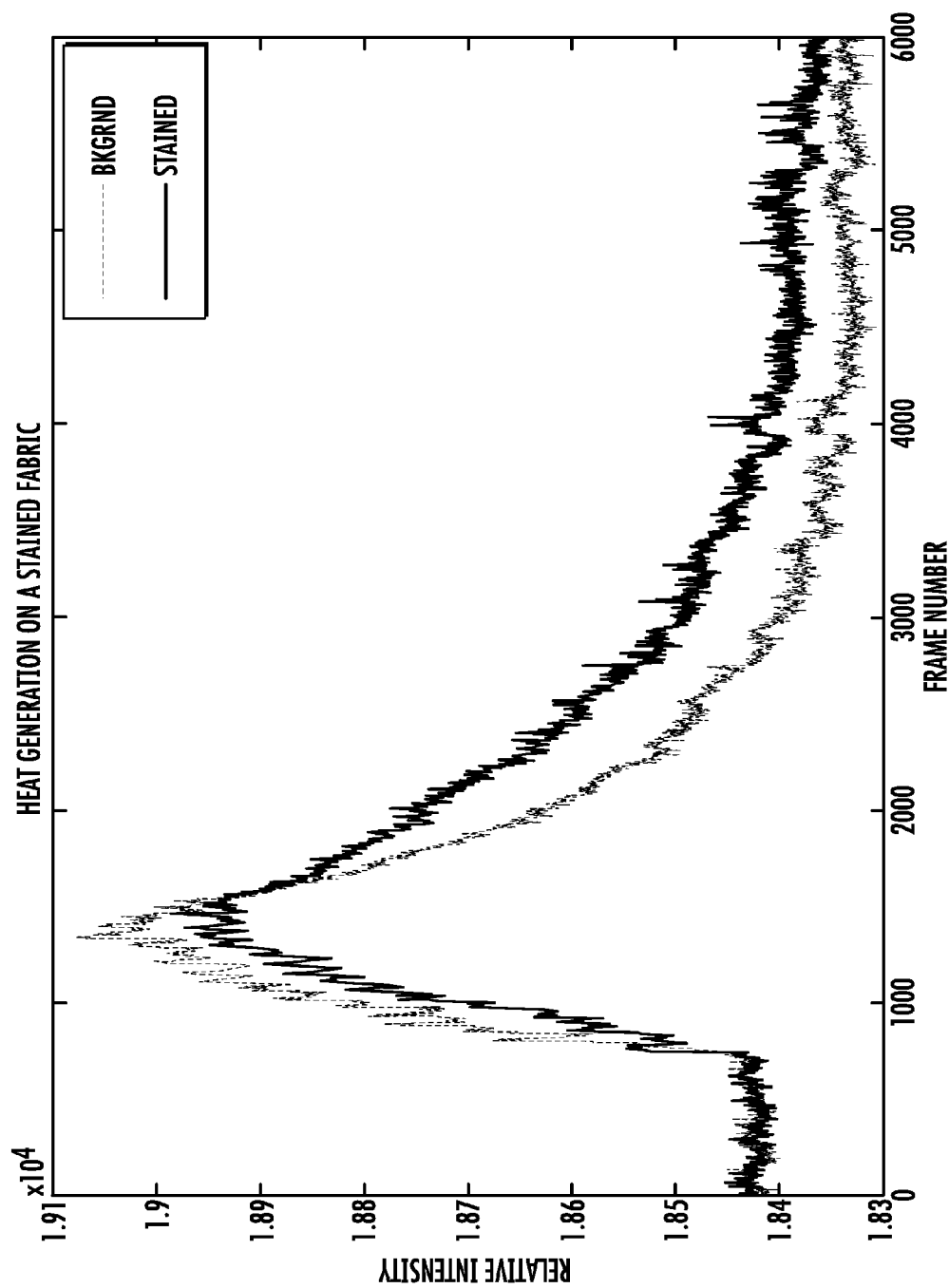
FIG. 1 shows the relatively humidity of the stained area compared to an area without a stain according to the Example.

Repeat use of reference characters in the present specification and drawings is intended to represent the same or analogous features or elements of the present invention.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Methods are generally provided for identifying chemical contrasts on a common surface(s). The presently disclosed methods can be used to detect "invisible" stains that are unseen by the human eye without using harsh chemicals or other damaging investigative techniques. The methods described herein can detect miniscule amounts of a substance on a surface.

Generally, the presence of a stain on a surface can be detected by applying a testing vapor (e.g., water, heavy water, an alcohol, an organic solvent, or a mixture thereof) onto the surface and monitoring the surface with an infrared camera that detects wavelengths of about 700 nm to about 1 mm (e.g., about 1 µm to about 25 µm) and/or a microbolometer that detects wavelengths of about 7.5 µm to about 14 µm.

Depending on the particular method utilized, the testing vapor can be applied to the surface with the substrate at room temperature (e.g., about 20° C. to about 25° C.) or pre-heated to a testing temperature (e.g., about 30° C. to about 65° C.).

I. Heating via the Testing Vapor

In one embodiment, the surface to be tested is heated via the testing vapor and then allowed to cool. For example, the surface can be heated from an initial temperature (e.g., from room temperature of about 20° C. to about 25° C.) to a peak temperature, and then allowed to cool back to the initial temperature. The peak temperature is, in most embodiments, relatively low so as to not substantially affect the surface being tested nor any biological material forming a stain thereon. For example, the peak temperature can be about 30° C. to about 65° C., such as about 30° C. to about 50° C.

In one embodiment, the peak temperature is no more than about 45° C. higher than the initial temperature, such as about 10° C. to about 40° C. higher than the initiation temperature. For example, when the initial temperature is at room temperature (e.g., about 20° C. to about 25° C.), the peak temperature can be about 30° C. to about 65° C., such as about 40° C. to about 60° C.

In certain embodiments, the peak temperature is no more than about 20° C. higher than the initial temperature, such as about 8° C. to about 15° C. higher than the initiation temperature (e.g., about 8° C. to about 10° C. higher than the initiation temperature). For example, when the initial temperature is at room temperature (e.g., about 20° C. to about 25° C.), the peak temperature can be about 30° C. to about 45° C., such as about 30° C. to about 40° C.

As stated, heating is achieved by applying a testing vapor onto the surface. The testing vapor can be any suitable solvent (or solvent system) that is easily and safely vaporized, since boiling is required to create the steam and/or the evaporation process. Also, depending on the composition surface and/or the anticipated composition of any latent stain present on the surface, the testing vapor should not readily solubilize either the surface or the stain. Particularly suitable testing vapors can include but are not limited to water, heavy water, an alcohol (e.g., methanol, ethanol, propanol, isopropanol, butanol, or a mixture thereof), an organic solvent, or a mixture thereof. For example, suitable organic solvents can include non-polar organic solvents (e.g., pentane, cyclopentane, hexane, benzene, toluene, chloroform, diethyl ether, etc.), polar aprotic organic solvents (e.g., dichloromethane, tetrahydrofuran, ethyl acetate, acetone, acetonitrile, etc.), polar protic solvents (e.g., alcohols, nitromethane, etc.), or mixtures thereof.

The testing vapor, in one preferred embodiment, comprises water ($H_2O$) and/or heavy water (also known as deuterium oxide, $D_2O$), due to their relatively low boiling points (100° C. and 101.4° C., respectfully) and their relatively mild affect, especially compared to certain organic solvents. For example, water and/or heavy water can be the primary constituent of the testing vapor, such that at least 50% by volume of the testing vapor. In one particular embodiment, the testing vapor can contain water and/or heavy water in an amount of about 90% by volume to 100% by volume (e.g., about 95% by volume to 100% by volume). For instance, the testing vapor can consist essentially of water and/or heavy water, being substantially free from any other gaseous material. As used herein, the term "substantially free" means no more than an insignificant trace amount present and encompasses completely free (e.g., 0% by volume up to 0.1% by volume).

Since the surface and the latent stain have different hydrophilic properties, the testing vapor (e.g., water and/or heavy water) adsorbs onto some substrates easier than others and then vaporizes/evaporates from some substrates easier than others. Thus, during heating and subsequent cooling utilizing the testing vapor, monitoring the surface with a temperature measuring instrument (e.g., an infrared camera) can detect a difference between areas on the surface. Thus, the stain becomes easily visible to the instrument operator.

During heating and/or subsequent cooling, the surface is monitored by a temperature measuring instrument (e.g., an infrared camera). The instrument records temperature measurements over time across the surface (e.g., utilizing relatively small pixels to ensure precise measurements). In the presence of a surface stain, the heating/cooling process of an area with a stain on the surface will differ from areas without a stain. Upon detection, the area where a stain is detected can be marked for further testing. If the area tested does not have a stain, it is observed that the treated regions show adsorption/desorption process to be substantially equivalent/uniform across the surface. Alternatively, if the area tested has a stain present, it is observed that the stained region(s) shows the adsorption/desorption process to be substantially different than the other, unstained areas/portions of the surface.

In one embodiment, the temperature measuring instrument is an infrared camera that detects wavelengths of about 700 nm to about 1 mm. In one particular embodiment, a relatively narrow wavelength range within the infrared spectrum can be monitored, such as about 1 µm to about 25 µm (e.g., about 7.5 µm to about 14 µm). For example, a microbolometer can be used as the temperature measuring instrument to detect infrared radiation within wavelengths of about 7.5 µm to about 14 µm. Such a microbolometer detects the infrared radiation that strikes the detector within the microbolometer, which heats it, and thus changes its electrical resistance. This resistance change is measured and processed into temperatures which can be used to create an image.

Heating of the surface can be achieved with relatively small amount of testing vapor within a short treatment time in order to minimize the impact on the surface and/or stain. In one embodiment, heating is achieved during a period of about 1 minute or less. For instance, heating can be performed for about 0.1 second to about 30 seconds, such as about 0.1 second to about 10 seconds. In one embodiment, the volume of liquid (e.g., water) utilized to form testing vapor during heating is less than about 25 mL/$m^2$, such as in the range of about 10 mL/$m^2$ to about 25 mL/$m^2$ (e.g., about 15 mL/$m^2$ to about 20 mL/$m^2$).

Figure 2:
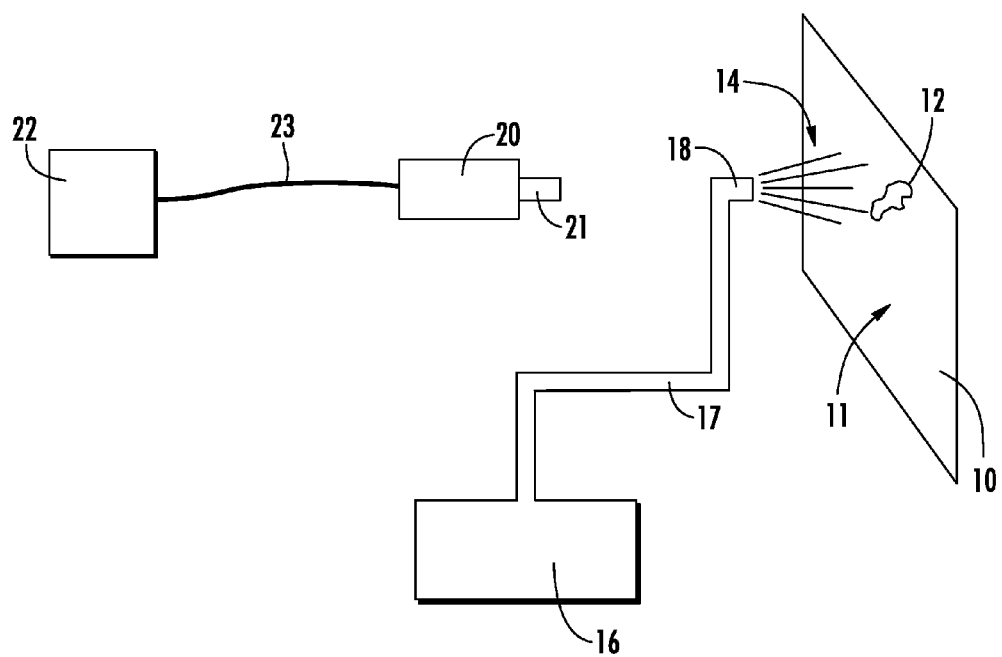
FIG. 2 shows an exemplary system for use in testing a surface of a substrate.

Referring to FIG. 2, a substrate 10 is shown defining a surface 11 with a latent stain 12 thereon. Testing vapor 14 is applied onto the surface 11 via a steamer 16 connected to a steam head 18 via a tube 17. A temperature measuring instrument 20 (e.g., an infrared camera) is shown monitoring the temperature of the surface 11 during application of the testing vapor 14 through lens 21. The temperature measuring instrument 20 is connected to a computing device 22 via connection 23 (e.g., a wire, wireless connections, etc.) in order to process the data collected by the temperature measuring instrument 20.

II. Pre-Heating the Substrate Followed by Applying Water Vapor

In another embodiment, the surface to be tested is preheated with a dry gas to a testing temperature, and then exposed to the testing vapor. Generally, the dry gas is substantially free from the component(s) of the testing vapor. That is, if the testing vapor is mainly water vapor, then the dry gas is substantially free from water.

For example, the substrate can be heated to the testing temperature (e.g., about 30° C. to about 65° C.) without the testing vapor present. Then, the substrate is exposed to the testing vapor, with the testing vapor having a temperature of within about 10% of the testing temperature. That is, if the testing temperature of the substrate is about 50° C., then the testing vapor can have a temperature of about 45° C. to about 55° C. Due to the relative similar (or, in a particular embodiment, substantially identical) temperature of the substrate and the testing vapor, the interaction of the testing vapor and the substrate is a substantially isothermal interaction. Thus, the effect of the interaction of the testing vapor and any stain on the surface of the substrate is monitored without any substantial change in temperature.

It was found that increasing the testing temperature in such a substantially isothermal interaction between the testing vapor and the substrate (and any stain thereon) intensifies the signal detected by the measuring instrument (e.g., an infrared camera). As such, the testing temperature of the substrate can be relatively high in preferred embodiments, such as about 50° C. to about 65° C., while still preventing degradation, evaporation, or another unwanted affect to any stain present on the substrate.

In certain embodiments, the substrate can heated (via the dry gas) to the testing temperature, exposed to the testing vapor at the testing temperature, and then allowed to cool back to a reduced temperature (e.g., room temperature), either in the presence or absence of the testing vapor. This process can be repeated for sufficient testing of the substrate.

As discussed above, the testing vapor can be any suitable solvent (or solvent system) that is easily and safely vaporized, since boiling is required to create the steam and/or the evaporation process. Also, depending on the composition surface and/or the anticipated composition of any latent stain present on the surface, the vapor should not readily solubilize either the surface or the stain. Particularly suitable vapors can include but are not limited to water, heavy water, an alcohol (e.g., methanol, ethanol, propanol, isopropanol, butanol, or a mixture thereof), an organic solvent, or a mixture thereof. For example, suitable organic solvents can include non-polar organic solvents (e.g., pentane, cyclopentane, hexane, benzene, toluene, chloroform, diethyl ether, etc.), polar aprotic organic solvents (e.g., dichloromethane, tetrahydrofuran, ethyl acetate, acetone, acetonitrile, etc.), polar protic solvents (e.g., alcohols, nitromethane, etc.), or mixtures thereof.

In one particular embodiment, water ($H_2O$) and/or heavy water (also known as deuterium oxide, $D_2O$) is utilized due to their relatively low boiling points (100° C. and 101.4° C., respectfully) and their relatively mild affect, especially compared to certain organic solvents.

Since the surface and the latent stain have different hydrophilic properties, the vapor (e.g., water and/or heavy water) adsorbs onto some substrates easier than others and then vaporizes/evaporates from some substrates easier than others. Thus, during exposure to the testing vapor, monitoring the surface with a temperature measuring instrument (e.g., an infrared camera) can detect a difference between areas on the surface. Thus, the stain becomes easily visible to the instrument operator.

During exposure to the testing vapor, the surface is monitored by a temperature measuring instrument (e.g., an infrared camera). The instrument records temperature measurements over time across the surface (e.g., utilizing relatively small pixels to ensure precise measurements). In the presence of a surface stain, the exposure of the testing vapor to an area with a stain on the surface will differ from areas without a stain. Upon detection, the area where a stain is detected can be marked for further testing. If the area tested does not have a stain, it is observed that the treated regions show adsorption/desorption process to be substantially equivalent/uniform across the surface. Alternatively, if the area tested has a stain present, it is observed that the stained region(s) shows the adsorption/desorption process to be substantially different than the other, unstained areas/portions of the surface.

In one embodiment, the temperature measuring instrument is an infrared camera that detects wavelengths of about 700 nm to about 1 mm. In one particular embodiment, a relatively narrow wavelength range within the infrared spectrum can be monitored, such as about 1 µm to about 25 µm (e.g., about 7.5 µm to about 14 µm). For example, a microbolometer can be used as the temperature measuring instrument to detect infrared radiation within wavelengths of about 7.5 µm to about 14 µm. Such a microbolometer detects the infrared radiation that strikes the detector within the microbolometer, which heats it, and thus changes its electrical resistance. This resistance change is measured and processed into temperatures which can be used to create an image.

The testing method can be achieved with relatively small amount of testing vapor within a short treatment time in order to minimize the impact on the surface and/or stain. In one embodiment, exposure to the testing vapor is achieved during a period of about 1 minute or less. For instance, exposure to the testing vapor can be performed for about 0.1 second to about 30 seconds, such as about 0.1 second to about 10 seconds. In one embodiment, the volume of liquid (e.g., water) utilized to form testing vapor during exposure is less than about 25 mL/m$^2$, such as in the range of about 10 mL/m$^2$ to about 25 mL/m$^2$ (e.g., about 15 mL/m$^2$ to about 20 mL/m$^2$).

Figure 3:
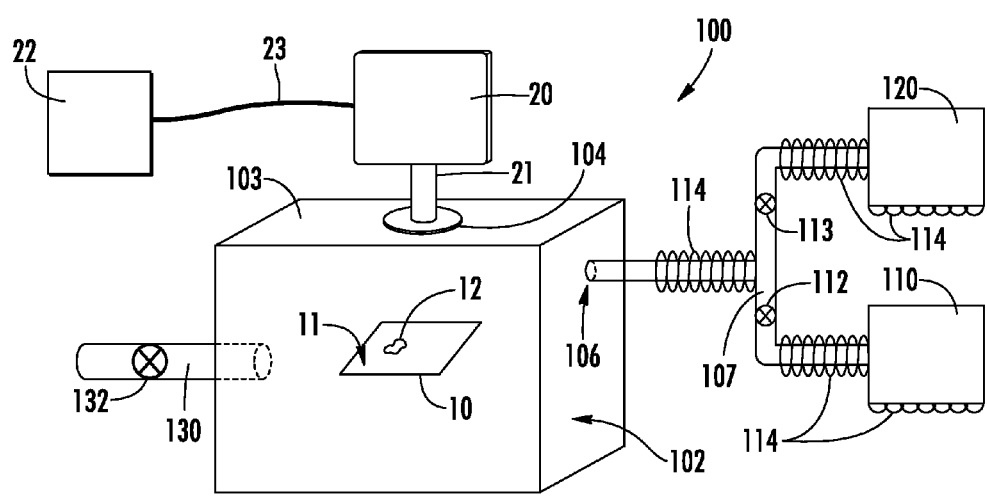
FIG. 3 shows another exemplary system for use in testing a surface of a substrate.

Referring to FIG. 3, an exemplary apparatus 100 is shown that can be utilized to perform the method of preheating the substrate with a dry gas to a testing temperature and exposing the substrate to the testing vapor, while monitoring the surface of the substrate with a temperature monitoring instrument (e.g., an IR camera).

Generally, a substrate 10 is shown defining a surface 11 with a latent stain 12 thereon. The substrate 10 is shown loaded into a closed chamber 102 that can be isolated from the surrounding atmosphere. A window 104 is shown in a wall 103 to allow the temperature monitoring instrument 20 to monitor the surface 11 of the substrate 10. For instance, the window 104 can be configured to be transparent to the wavelengths monitored by the temperature monitoring instrument 20 (e.g., IR wavelengths). In one embodiment, the window 104 can be, for instance, a polyethylene film that is transparent to IR wavelengths.

A dry gas source 110 (e.g., a tank, reservoir, etc.) is configured to supply the dry gas to the chamber 102 via gas inlet 106 and associated piping 107. Gas valve 112 is positioned within the piping 107 to control the flow of the dry gas into the chamber 102. A heating mechanism 114 is shown positioned to heat the dry gas within the dry gas source 110 and/or the piping 107. As such, the dry gas can be heated to the testing temperature prior to exposure to the substrate 10 within the chamber 102. Thus, the substrate 10 can be preheated to the testing temperature within the chamber 102 utilizing the dry gas.

A testing vapor source 120 (e.g., a tank, reservoir, etc.) is configured to supply the testing vapor to the chamber 102 via gas inlet 106 and associated piping 107. Gas valve 113 is positioned within the piping 107 to control the flow of the testing vapor into the chamber 102. A heating mechanism 114 is shown positioned to heat the vapor source within the testing vapor source 120 and/or the piping 107. As such, the testing vapor source (which may be a liquid) can be heated to form the testing vapor within the vapor source 120 and then kept at the testing temperature within the piping 107 prior to exposure to the substrate 10 within the chamber 102. Thus, the substrate 10 can be exposed to the testing vapor at the testing temperature within the chamber 102 so as to have a substantially isothermal interaction therewith.

An exit pipe 130 is shown on the opposite side of the chamber 102 from the inlet 106 so as to create a flow of gas (either the dry gas, the testing vapor, or a mixture thereof) past the substrate 10 during testing. An exit valve 132 is configured to control the flow of gas out of the chamber 102.

Of course, any suitable system or apparatus can be utilized to perform the disclosed methods, other than the exemplary apparatus 100 shown in FIG. 3.

EXAMPLES

A small steamer (Rowenta GS2010 UltraSteam Handheld Fabric Steamer) was utilized to heat a surface in search of latent stains. An infrared camera (specifically a microbolometer detecting wavelengths of about 8 μm to about 14 μm (FLIR A-315, available from FLIR Systems, Inc., Portland, Oreg.), which responds to temperature change, was used to make active thermographic measurements on the surface. As the surface was exposed to steam (water vapor), the surface is heated from room temperature. In this example, the steam was exposed to an area of about one square foot of the surface for a time frame of about 8 seconds to about 12 seconds. About 2 mL to about 3 mL of water was utilized to form the vapor during the heating process. Thus, the volume of water utilized to form vapor during heating was in the range of about 15 mL/$m^2$ to about 20 mL/$m^2$ (calculated using about 0.16 mL/second for 10 seconds over a 1 sq ft area (0.0929 $m^2$).

Once the steaming has ceased, the surface temperature of the surface began to decrease to equilibrium. FIG. 1 shows the results of this heating and cooling process from a stained area compared to an area without a stain (referred to as the background). The first 800 frames were recorded so that the equilibrium point is known. The increase in pixel value is caused by exposure to steam/adsorption of water molecules on the surface of the test fabric. These molecules are at higher temperature than the surface of the fabric which is observed by the infrared camera.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claim

What is claimed:

1. A method for detecting a chemical contrast on a surface, the method comprising: heating the surface with a testing vapor from an initial temperature to a peak temperature, allowing the surface to cool from the peak temperature to the initial temperature, and monitoring the surface with a temperature measuring instrument during heating, wherein any portion of the surface that heats differently than the remaining portion of the surface indicates a stain is present, and wherein the temperature measuring instrument comprises an infrared camera or a microbolometer.

2. The method as in claim 1, further comprising:
monitoring the surface with a temperature measuring instrument during cooling, wherein any portion of the surface that cools differently than the remaining portion of the surface indicates a stain is present.

3. The method as in claim 1, wherein the vapor comprises water, heavy water, an alcohol, an organic solvent, or a mixture thereof.

4. The method as in claim 1, wherein the vapor comprises an alcohol, wherein the alcohol comprises methanol, ethanol, propanol, isopropanol, butanol, or a mixture thereof.

5. The method as in claim 1, wherein the temperature measuring instrument comprises an infrared camera that detects wavelengths of about 700 nm to about 1 mm.

6. The method as in claim 1, wherein the temperature measuring instrument comprises an infrared camera that detects wavelengths of about 1 μm to about 25 μm.

7. The method as in claim 1, wherein the temperature measuring instrument comprises a microbolometer that detects wavelengths of about 7.5 μm to about 14 μm.

8. The method as in claim 1, wherein the initial temperature is about 20° C. to about 25° C.

9. The method as in claim 1, wherein heating is performed for about 1 minute or less.

10. The method as in claim 1, wherein heating is performed for about 0.1 second to about 30 seconds.

11. The method as in claim 1, wherein the peak temperature is about 30° C. to about 50° C.

12. The method as in claim 1, wherein the amount of vapor applied during heating is about 25 mL/$m^2$ or less.

13. A method for detecting a chemical contrast on a surface, the method comprising: heating the surface with a vapor from an initial temperature to a peak temperature, allowing the surface to cool from the peak temperature to the initial temperature, and monitoring the surface with a temperature measuring instrument during cooling, wherein the temperature measuring instrument comprises an infrared camera or a microbolometer, and wherein any portion of the surface that cools differently than the remaining portion of the surface indicates a stain is present.

14. A method for detecting a chemical contrast on a surface of a substrate, the method comprising: preheating the substrate to a testing temperature, exposing the substrate to a testing vapor, monitoring the surface of the substrate with a temperature measuring instrument during exposure to the testing vapor, wherein the temperature measuring instrument comprises an infrared camera or a microbolometer, and wherein any portion of the surface that shows a thermal event different than the remaining portion of the surface indicates a stain is present.

15. The method as in claim 14, wherein preheating the substrate to the testing temperature comprises: exposing the substrate to a dry gas that has a gas temperature that is at or above the testing temperature.

16. The method as in claim 14, wherein preheating the substrate to the testing temperature is achieved in the absence of the testing vapor.

17. The method as in claim 14, wherein the testing temperature is about 50° C. to about 65° C.

18. The method as in claim 14, wherein the vapor comprises water, heavy water, an alcohol, an organic solvent, or a mixture thereof.

19. The method as in claim 14, wherein the temperature measuring instrument comprises an infrared camera that detects wavelengths of about 700 nm to about 1 mm.

20. The method as in claim 14, wherein the temperature measuring instrument comprises a microbolometer that detects wavelengths of about 7.5 μm to about 14 μm.

* * * * *